United States Patent [19]

Köppe et al.

[11] 4,442,120
[45] Apr. 10, 1984

[54] 1-ARYLOXY-3-ALKYLAMINO-PROPAN-2-OLS

[75] Inventors: Herbert Köppe; Werner Kummer; Helmut Stähle; Gojko Muacevic; Werner Traunecker, all of Ingelheim, Fed. Rep. of Germany

[73] Assignee: Boehringer Ingelheim KG, Ingelheim am Rhein, Fed. Rep. of Germany

[21] Appl. No.: 398,577

[22] Filed: Jul. 15, 1982

[30] Foreign Application Priority Data

Aug. 26, 1981 [DE] Fed. Rep. of Germany ....... 3133678

[51] Int. Cl.³ .............. A61K 31/36; A61K 31/275; C07C 121/80; C07D 317/60
[52] U.S. Cl. ............................. 424/282; 260/465 D; 424/304; 549/436
[58] Field of Search .................. 260/465 D; 424/304, 424/282; 549/436

[56] References Cited

U.S. PATENT DOCUMENTS 3,712,927  1/1973  Howe et al. ............... 260/465 E X Primary Examiner—Dolph H. Torrence
Attorney, Agent, or Firm—Hammon & Littell, Weissenberger & Dippert

[57] ABSTRACT

Compounds of the formula

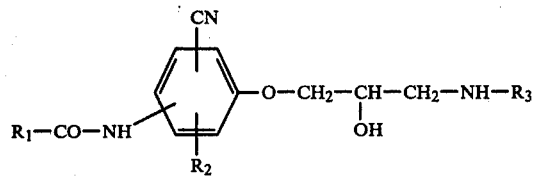

wherein $R_1$ is cycloalkyl of 3 to 10 carbon atoms; phenyl; mono- or poly-substituted phenyl, where the substituents are halogen, lower alkyl, lower alkoxy, lower alkenyl, lower alkinyl, lower alkinyloxy, lower cycloalkyl, acyl, acyloxy, lower alkoxycarbonyl, hydroxy-lower alkyl, lower alkoxy-lower alkyl or the ring-forming groups (—CH=CH—)$_2$ or —O—CH$_2$—O— attached to vicinal carbon atoms of the phenyl ring; aryloxy-lower alkyl; (mono- or poly-substituted aryl)-oxy-lower alkyl, where the substituents are halogen, lower alkyl, lower alkoxy, lower alkenyl, lower alkinyl, lower alkinyloxy, lower cycloalkyl, acyl, acyloxy, lower alkoxycarbonyl, hydroxy-lower alkyl, lower alkoxy-lower alkyl or the ring-forming groups (—CH=CH—)$_2$ or —O—CH$_2$—O— attached to vicinal carbon atoms of the phenyl ring;

$R_2$ is hydrogen, halogen, alkyl of 1 to 4 carbon atoms, alkoxy of 1 to 4 carbon atoms or the ring-forming group (—CH=CH—)$_2$ or —(CH$_2$)$_n$—, where n is an integer from 3 to 5, attached to vicinal carbon atoms of the phenyl ring; and $R_3$ is straight or branched alkyl of 1 to 10 carbon atoms;

and non-toxic, pharmacologically acceptable acid addition salts thereof. The compounds as well as their salts are useful for the treatment of tachycardia, hypertension and coronary diseases.

9 Claims, No Drawings

1-ARYLOXY-3-ALKYLAMINO-PROPAN-2-OLS

This invention relates to novel 1-aryloxy-3-alkylamino-propan-2-ols and non-toxic acid addition salts thereof, to methods of preparing these compounds, to pharmaceutical compositions containing them as active ingredients, and to methods of using them for the treatment of coronary heart diseases, cardiac arrhythmia and hypertension.

More particularly, the present invention relates to a novel class of compounds represented by the formula

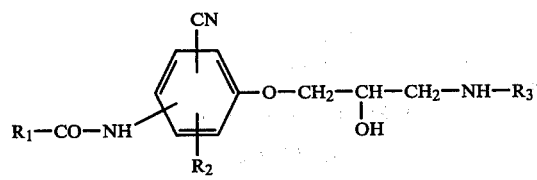

wherein
- $R_1$ is cycloalkyl of 3 to 10 carbon atoms; phenyl; mono- or poly-substituted phenyl, where the substituents are halogen, lower alkyl, lower alkoxy, lower alkenyl, lower alkinyl, lower alkinyloxy, lower cycloalkyl, acyl, acyloxy, lower alkoxycarbonyl, hydroxy-lower alkyl, lower alkoxy-lower alkyl or the ring-forming groups (—CH=CH—)$_2$ or —O—CH$_2$—O— attached to vicinal carbon atoms of the phenyl ring; aryloxy-lower alkyl; (mono- or poly-substituted aryl)-oxy-lower alkyl, where the substituents are halogen, lower alkyl, lower alkoxy, lower alkenyl, lower alkinyl, lower alkinyloxy, lower cycloalkyl, acyl, acyloxy, lower alkoxycarbonyl, hydroxy-lower alkyl, lower alkoxy-lower alkyl or the ring-forming groups (—CH=CH—)$_2$ or —O—CH$_2$—O— attached to vicinal carbon atoms of the phenyl ring;
- $R_2$ is hydrogen, halogen, alkyl of 1 to 4 carbon atoms, alkoxy of 1 to 4 carbon atoms or the ring-forming group (—CH=CH)$_2$ or —(CH$_2$)$_n$—, where n is an integer from 3 to 5, attached to vicinal carbon atoms of the phenyl ring; and
- $R_3$ is straight or branched alkyl of 1 to 10 carbon atoms;

and non-toxic, pharmacologically acceptable acid addition salts thereof.

A preferred subgenus is constituted by compounds of the formula I wherein
- $R_1$ is substituted phenoxy-methyl or lower cycloalkyl, especially cyclobutyl,
- $R_2$ is hydrogen, and
- $R_3$ is alkyl branched adjacent to the amino group, especially isopropyl or tert. butyl, and non-toxic, pharmacologically acceptable acid addition salts thereof.

The compounds embraced by formula I may be prepared by the following methods:

Method A

By reacting a compound of the formula

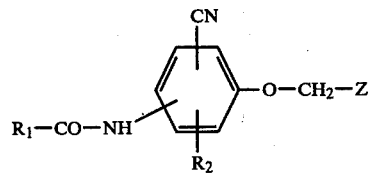

wherein
$R_1$ and $R_2$ have the meanings previously defined, and Z is

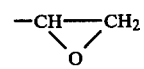

or —CH(OH)—CH$_2$—Hal, where Hal is halogen, with an amine of the formula $$H_2N—R_3 \qquad (III)$$

wherein $R_3$ has the meanings previously defined.

Method B

By hydrolyzing an oxazolidine derivative of the formula

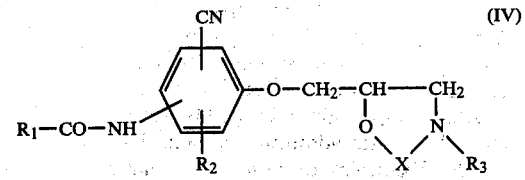

wherein
$R_1$, $R_2$ and $R_3$ have the meanings previously defined, and
X is —CO—, —CH$_2$— or

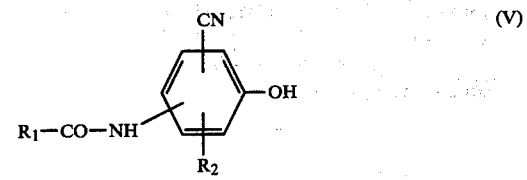

alkyl, for example with sodium hydroxide or potassium hydroxide in water or in a mixture of ethanol and water.

Method C

By reacting a compound of the formula

wherein $R_1$ and $R_2$ have the meanings previously defined, or a salt of this phenol, with an azetidinol derivative of the formula

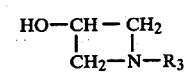

wherein $R_3$ has the meanings previously defined, in an anhydrous medium and in the presence of an alkali.

The starting compounds of the formulas II and III are known compounds.

The oxazolidinone starting compounds of the formula IV, i.e. where X is —CO—, may for example be prepared by reacting an epoxide of the formula II with a urethane of the formula $$R_3-HN-\underset{\underset{O}{\|}}{C}-OC_2H_5 \qquad (VII)$$

wherein $R_3$ has the meanings previously defined, which, in turn, may be prepared from ethyl chloroformate and an amine of the formula III.

The preparation of the starting compounds of the formula IV where X is —CH$_2$— or —C—lower alkyl is described in the literature.

The preparation of the phenol starting compounds of the formula V is also described in the literature.

The azetidinol starting compounds of the formula VI may be prepared by the method described in Chem.-Pharm.Bull. (Japan), Vol. 22(7), 1974, page 1490.

The compounds of the present invention have an asymmetric carbon atom at the —CH(OH)—group and therefore occur both as racemates and in the form of the optical antipodes. The latter may be obtained not only by separation of the racemates with conventional auxiliary acids such as dibenzoyl- (or di-p-toluyl-) D-tartaric acid or D-3-bromocamphor-8-sulfonic acid, but also by using optically active starting material.

The compounds embraced by formula I are basic and therefore form addition salts with inorganic or organic acids. Examples of non-toxic, pharmacologically acceptable acid addition salts are those formed with hydrochloric acid, hydrobromic acid, sulfuric acid, methanesulfonic acid, maleic acid, acetic acid, oxalic acid, lactic acid, tartaric acid, 8-chlorotheophylline or the like.

The following examples illustrate the present invention and will enable others skilled in the art to understand it more completely. It should be understood, however, that the invention is not limited solely to the particular examples given below.

EXAMPLE 1

1-[2-Cyano-4-(3'-methylphenoxyacetylamino)-phenoxy]-3-tert.butylamino-propan-2-ol

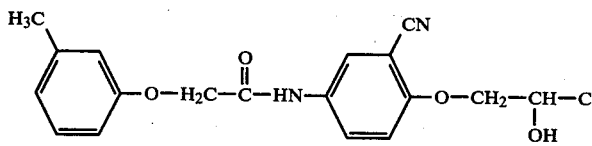

7 gm (0.021 mol) of 1-[2-cyano-4-(3'-methylphenoxyacetylamino)-phenoxy]-2,3-epoxy-propane were dissolved in 80 ml of ethanol and, after the addition of 2.2 ml (0.021 mol) of tert. butylamine, the mixture was refluxed for 90 minutes. After the solvent had been distilled off, the residue was digested with ethyl acetate, and the solid fraction was separated by suction filtration. The base thus obtained in the form of fine crystals was recrystallized twice from ethyl acetate by adding hexane.

Yield: 2.6 gm. Melting point: 130°–131° C.

EXAMPLE 2

1-(2-Cyano-4-cyclobutylcarbonylamino-phenoxy)-3-tert. butylamino-propan-2-ol 7.5 gm (0.024 mol) of 1-(2-cyano-4-cyclobutylcarbonylamino-phenoxy)-3-chloro-propan-2-ol were dissolved in 80 ml of ethanol, and the solution was mixed with 8.7 gm (0.12 mol) of tert. butylamine, and the mixture was refluxed for four hours. The solvent was distilled off in vacuo, the residue was extracted by shaking with dilute hydrochloric acid with the addition of ether, and the organic phase was separated. The aqueous phase was washed with ether and made alkaline with NH$_4$OH. The base which precipitated was extracted with ethyl acetate, and the organic phase was dried over MgSO$_4$. The ethyl acetate was distilled off, and the crystalline residue was recrystallized twice from acetonitrile.

Yield: 5.7 gm. Melting point: 110°–113° C.

EXAMPLE 3

1-[2-Cyano-4-(4'-chlorobenzoylamino)-phenoxy]-3-tert. butylamino-propan-2-ol 12 gm of 1-[2-Cyano-4-(4'-chlorobenzoylamino)-phenoxy]-3-chloro-propan-2-ol were dissolved in 100 ml of ethanol, 15 ml of tert. butylamine were added, and the mixture was refluxed for three hours. After the ethanol had been distilled off, the residue was acidified with dilute hydrochloric acid, the aqueous solution was extracted by shaking with ether, and the aqueous phase was made alkaline with NaOH. The base thus obtained was taken up in ethyl acetate, the organic phase was washed with water and dried over Na$_2$SO$_4$, and the solvent was distilled off. The residue was purified on a silica gel column. The solid base was recrystallized from isopropanol.

Yield: 4 gm. Melting point: 182°–183° C.

EXAMPLE 4

1-[2-Cyano-4-(4'-methylbenzoylamino)-phenoxy]-3-isopropylamino-propan-2-ol hydrochloride 3 gm (0.009 mol) of 1-[2-cyano-4-(4'-methylbenzoylamino)-phenoxy]-3-chloro-propan-2-ol were dissolved in 80 ml of ethanol, 3.8 ml (0.045 mol) of isopropylamine were added to the solution, and the mixture was refluxed for two hours. After the methanol had been distilled off, the residue was dissolved in hydrochloric acid, the solution was extracted with ethyl acetate, and the aqueous phase was made alkaline with NaOH. The free base thus obtained was extracted several times with ethyl acetate, and after washing the extracted solution with water it was dried over Na$_2$SO$_4$. By distilling off the ethyl acetate, a residue was obtained which was digested with acetonitrile, then suction-filtered, and the filter cake was suspended in acetonitrile. After the addition of ethanolic HCl, a solution was formed. The addition of ether thereto initiated the crystallization of the hydrochloride, which was accelerated by cooling. The hydrochloride was recrystallized by dissolving it in ethanol and adding ether.

Yield: 2 gm. Melting point: 193°–195° C.

EXAMPLE 5

1-[2-Cyano-4-(4'-methoxybenzoylamino)-phenoxy]-3-tert. butylamino-propan-2-ol 14 gm of 1-[2-cyano-4-(4'-methoxybenzoylamino)-phenoxy]-3-chloro-propan-2-ol were dissolved in 100 ml of ethanol, 20 ml of tert. butylamine were added to the solution, and the mixture was refluxed for 4 hours. After the ethanol had been distilled off, the residue was dissolved in dilute hydrochloric acid, the solution was extracted by shaking with ether, the aqueous phase was made alkaline with NaOH, and the free base thus obtained was taken up in ethyl acetate. The organic phase was washed with water, dried over $NA_2SO_4$, the ethyl acetate was distilled off, and the residue was purified on a silica gel column (ethyl acetate/isopropanol/$NH_4OH$ 70:30:5). The base thus isolated was recrystallized from ethyl acetate by the addition of petroleum ether (boiling point 40° C.).

Yield: 3.2 gm. Melting point: 108°–110° C.

Using a procedure analogous to that described in Example 2, the compounds of the formula

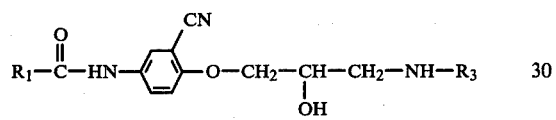

shown in the following table were also prepared from the corresponding p-acylamino-1-phenoxy-2-hydroxy-3-chloropropane of the formula II and the corresponding alkylamine of the formula III by refluxing in ethanol:

| Example No. | $R_1$ | $R_3$ | Melting point °C. (hydrochloride unless otherwise stated) |
|---|---|---|---|
| 6 |  | tert. $C_4H_9$ | 165–166 |
| 7 |  | tert. $C_4H_9$ | 117–120 |
| 8 |  | iso $C_3H_7$ | 159–162 (Base) |
| 9 |  | sec. $C_4H_9$ | 127–130 (Base) |
| 10 |  | iso $C_3H_7$ | 214–216 |
| 11 |  | tert. $C_4H_9$ | 151–152 (Base) |
| 12 | 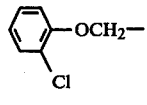 | tert. $C_4H_9$ | 124–125 (Base) |
| 13 | 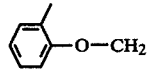 | iso $C_3H_7$ | 130–131 (Base) |
| 14 | 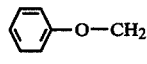 | sec. $C_4H_9$ | 139–140 (Base) |
| 15 | 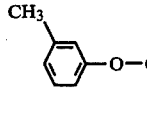 | iso $C_3H_7$ | 172–173 |
| 16 | 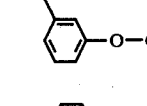 | sec. $C_4H_9$ | 134–135 (Base) |
| 17 | 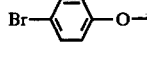 | iso $C_3H_7$ | 240–242 |
| 18 | 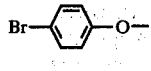 | sec. $C_4H_9$ | 216–218 |
| 19 | 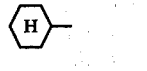 | iso $C_3H_7$ | 142–143 (Base) |
| 20 | 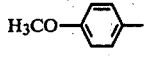 | iso $C_3H_7$ | 157–159 (Base) |
| 21 | 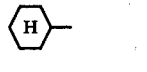 | tert. $C_4H_9$ | 143–144 |
| 22 | 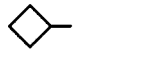 | iso $C_3H_7$ | 120–123 (Base) |
| 23 |  | iso $C_3H_7$ | 158–159 (Base) |
| 24 |  | tert. $C_4H_9$ | 121–124 (Base) |
| 25 | 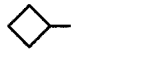 | sec. $C_4H_9$ | 83–86 (Base) |
| 26 | 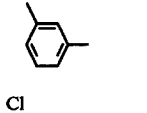 | tert. $C_4H_9$ | 182–184 |
| 27 | 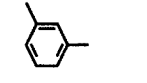 | iso $C_3H_7$ | 194–196 |
| 28 | 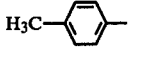 | tert. $C_4H_9$ | 155–158 |

-continued

| Example No. | $R_1$ | $R_3$ | Melting point °C. (hydrochloride unless otherwise stated) |
|---|---|---|---|
| 29 | Cl—C$_6$H$_4$— | iso C$_3$H$_7$ | 164–165 (Base) |
| 30 | CH$_3$—C$_6$H$_4$— | iso C$_3$H$_7$ | 154–155 (Base) |
| 31 | CH$_3$—C$_6$H$_4$— | tert. C$_4$H$_9$ | 126–127 (Base) |
| 32 | F—C$_6$H$_4$— | tert. C$_4$H$_9$ | 191–193 (Base) |
| 33 | F—C$_6$H$_4$— | iso C$_3$H$_7$ | 203–205 |

The compounds of the present invention, that is, those embraced by formula I above and their non-toxic, pharmacologically acceptable acid addition salts, have useful pharmacodynamic properties. More particularly, they exhibit β-adrenolytic activities in warm-blooded animals such as guinea pigs, and are therefore useful, for example, for the treatment or prophylaxis of coronary heart disease, particularly angina pectoris, and for treating cardiac arrhythmia, more particularly tachycardia. The hypotensive properties and calcium-antagonistic effects of the compounds of the formula I are also therapeutically useful. In addition, the compounds have favorable metabolic properties. Compared with known β-receptor blockers, for instance the commercial product 1-(2-acetyl-4-butyroylamino-phenoxy)-3-isopropylamino-propan-2-ol (Acebutolol) which is of similar structure, the compounds of this invention have the advantage of greatly reduced toxicity, enhanced activity and exceptional organ selectivity.

The above pharmacological properties were ascertained by the following standard test methods:

1. Inhibition of Isoprenaline tachycardia (aludrine-antagonistic effect)

Method: Inhibition of the tachycardiac reaction to a standard dose of isoprenaline and effect on the basal heart rate by increasing i.v. doses of a β-adrenolytic.

Animals used: Male and female guinea pigs with body weights of 270 to 350 gm kept in a group, with standard food and water ad libitum until the beginning of the test. Food was withdrawn 16 hours before the start of the test.

Anesthesia: Ethyl urethane 1.75 gm/kg as a 20% solution administered intraperitoneally, re-injected if necessary.

Preparation: Cannulation of a Vena jugularis exterior for intravenous injection; insertion of a tracheal cannula and artificial respiration; subcutaneous needle electrodes for recording the ECG, generally in extremity lead II, recording rate 25 mm/sec; rectal thermometer for monitoring body temperature, which was kept constant at 34° to 36° C. with a heat lamp (infra-red radiator) by means of an automatic electronic device.

Test procedure: The heart rate was determined by counting the r waves in the ECG, in each case from a reducing time of 3 to 4 seconds. About 30 minutes after preparation, the normal heart rate was recorded 5 times at intervals of 2 minutes and averaged. Then, 1 μg/kg of isoprenaline was injected i.v. as an adrenergic stimulant, and thereafter the heart rate was recorded again every 30 seconds for 3 minutes. The injections of isoprenaline were repeated at 30 minute intervals throughout the test. When the spontaneous rate remained substantially constant and the tachycardiac reaction to the first 2 to 3 administrations of isoprenaline was uniform, the first dose of the test compound was injected i.v. 15 minutes after the previous isoprenaline reaction and 15 minutes before the next isoprenaline reaction. Further geometrically increasing doses of the test compound were administered at intervals of 60 minutes until there was a significant inhibition of the isoprenaline tachycardia.

2. Cardioselectivity in conscious guinea pigs

Principle: Conscious guinea pigs are exposed to a lethal dose of a histamine aerosol, using the method of D. Dunlop and R. G. Shanks [Brit. J. Pharmacol. 32, 201 (1968)]. The animals are protected from the lethal effect of the histamine by a pre-treatment with isoprenaline. A β-adrenolytic neutralizes the action of the isoprenaline, so that the protection from histamine bronchospasm is lost if the compound in question is not a cardioselective substance. If a β-adrenolytic compound effective in the heart does not show any antagonism towards isoprenaline in this test, cardioselectivity can be assumed (for so-colled $\beta_1$-receptors).

Animals used: Male and female guinea pigs (6 animals per dose), with body weights of 350 to 400 g, kept in a group. Given unlimited food and water until the start of the test. Food withdrawn 16 hours before the test began.

Test procedure: Groups of 6 animals (3 male and 3 female) were treated subcutaneously with 5 or more different doses of the β-adrenolytic. 15 minutes later they were given 0.1 mg/kg of isoprenaline contralaterally by subcutaneous injection. After a further 15 minutes, the animals were placed in a cylindrical chamber with a capacity of 2 liters and exposed for 45 seconds to an aqueous histamine aerosol (1.25%), and the mortality was then evaluated.

Evaluation: The lethality was plotted against the logarithm of the dose, and the LD$_{50}$ was determined by the method of J. Litchfield and F. Wilcoxon [J. Pharmacol. Exp. Therap. 96, 99–113, (1949)]. A selectivity quotient (LD$_{50}$/ED$_{50}$) was determined with the LD$_{50}$ from this test and the cardiac ED$_{50}$ from the test for the inhibition of iroprenaline tachycardia (on anesthetized guinea pigs). A compound is regarded as being cardioselective if the quotient is greater than 1.

Compounds of the formula I which have proved particularly useful are those wherein R$_3$ represents an isopropyl- or tert. butyl-amino group (substituted p-acylamino-1-phenoxy-3-isopropyl- or tert.butyl-amino-propan-2-ols). Particularly useful compounds are 1-[2-cyano-4-(3'-methylphenoxyacetylamino)-phenoxy]-3-tert.butyl-aminopropan-2-ol and 1-(2-cyano-4-cyclobutyl-carbonylaminophenoxy)-3-tert.butylamino-propan-2-ol and the non-toxic acid addition salts thereof.

For pharmaceutical purposes the compounds of the present invention are administered to warm-blooded animals perorally, parenterally or rectally as active ingredients in customary pharmaceutical compositions, that is, compositions consisting essentially of an inert pharmaceutical carrier and an effective amount of the active ingredient, such as tablets, coated tablets, solutions, emulsions, powders, capsules, suppositories and delayed release compositions, using the conventional pharmaceutical excipients and conventional methods of production.

Tablets may be produced, for example, by mixing the active ingredients with known excipients, for example inert diluents such as calcium carbonate, calcium phosphate or lactose, disintegrants such as corn starch or alginic acid, binders such as starch or gelatin, lubricants such as magnesium stearate or talc, and/or agents for obtaining delayed release, such as carboxy-polymethylene, carboxymethylcellulose, cellulose acetate phthalate, or polyvinyl acetate.

The tablets may consist of several layers. Coated tablets may be produced analogously by coating cores produced in the same way as the tablets with the agents conventionally used for coating tablets, e.g. collidone or shellac, gum arabic, talc, titanium dioxide or sugar. In order to obtain delayed release or avoid incompatibilities, the core may also consist of several layers. Similarly, the coating of the tablet may consist of several layers in order to obtain delayed release, for which the excipients mentioned above in respect of the tablets may be used.

Syrups of the active ingredients or combinations of active ingredients according to the invention may additionally contain a sweetener, such as saccharin, cyclamate, glycerin or sugar, and a flavor-improving agent, for instance a flavoring such as vanillin or orange extract. They may also contain suspension agents or thickeners, such as sodium carboxymethylcellulose, wetting agents, for example condensation products of fatty alcohols with ethylene oxide, or preservatives such as p-hydroxybenzoates.

Injection solutions are prepared in the usual way, for instance by adding preservatives such as p-hydroxybenzoates or stabilizers such as complexones, and filling them into injection vials or ampules.

Capsules containing the active ingredients or combinations of active ingredients may be prepared, for example, by mixing the active ingredients with inert carriers such as lactose or sorbitol and then filling gelatin capsules with the mixture.

Suitable suppositories may be prepared, for example, by mixing the active ingredients or combinations of active ingredients intended therefor with conventional carriers such as neutral fats of polyethyleneglycol or derivatives thereof.

The compounds of this invention are also suitable for administration in combination with other pharmacodynamically active compounds such as, for example, coronary dilators, sympathicomimetics, cardiac glycosides and tranquilizers.

An effective amount of the compounds of the present invention is 0.014 to 4.29 mgm/kg, preferably 0.071 to 1.43 mgm/kg body weight p.o., and 0.014 to 0.29 mgm/kg body weight parenterally.

The following examples illustrate a few pharmaceutical dosage unit compositions comprising a compound of the present invention as an active ingredient and represent the best modes contemplated of using the invention. The parts are parts by weight unless otherwise specified.

EXAMPLE 34

Tablets

The tablet composition is compounded from the following ingredients:

| | |
|---|---|
| 1-[2-Cyano-4-(3'-methylphenoxy-acetylamino)-phenoxy]-3-tert.butylamino-propan-2-ol | 40.0 parts |
| Corn starch | 164.0 parts |
| Sec. calcium phosphate | 240.0 parts |
| Magnesium stearate | 1.0 parts |
| | 445.0 parts |

Preparation:
The individual ingredients are thoroughly mixed together and the mixture is granulated in the usual way. The granulate is compressed into 445 mg-tablets, each containing 40 mg of the active ingredient.

EXAMPLE 35

Gelatin Capsules

The capsule filler composition is compounded from the following ingredients:

| | |
|---|---|
| 1-(2-Cyano-4-cyclobutylcarbonyl-amino-phenoxy)-3-(tert.butyl-amino)-propan-2-ol. HCl | 25 parts |
| Corn starch | 175 parts |
| | 200 parts |

Preparation:
The ingredients are thoroughly mixed, and 200 mg portions of the mixture are filled into gelatine capsules of suitable size. Each capsule contains 25 mg of the active ingredient.

EXAMPLE 36

Injection Solution

The solution is compounded from the following ingredients:

| | | |
|---|---|---|
| 1-[2-Cyano-4-(4'-methoxybenzoyl-amino)-phenoxy]-3-tert.butyl-amino-propan-2-ol | | 2.5 parts |
| Sodium salt of EDTA | | 0.2 parts |
| Distilled water | q.s.ad | 100.0 parts |

Preparation:
The active ingredient and the EDTA salt are dissolved in a sufficient amount of water, and the solution is diluted to the required volume with water. The solution is filtered to remove any suspended particles and then filled into 1 cc-ampules under aseptic conditions. Finally, the ampules are sterilized and sealed. Each ampule contains 25 mg of the active ingredient.

EXAMPLE 37

Delayed-Release Coated Tablets

The tablet core is compounded from the following ingredients:

| | |
|---|---|
| (−)-1-[2-Cyano-4-(3'-methylphenoxy-acetyl-amino)-phenoxy]-3-tert.butylamino-propan-2-ol | 25.0 parts |

-continued

| | |
|---|---|
| Carboxymethylcellulose (CMC) | 295.0 parts |
| Stearic acid | 20.0 parts |
| Cellulose acetate phthalate (CAP) | 40.0 parts |
| | 380.0 parts |

Preparation:

The active ingredient, the CMC and the stearic acid are thoroughly mixed, and the mixture is granulated in the usual way, using a solution of the CAP in 200 ml of a mixture of ethanol and ethyl acetate. The granulate is then compressed into 380 mg-tablet cores which are then coated in the usual way with s sugar-containing 5% solution of polyvinylpyrrolidone in water. Each coated tablet contains 25 mg of the active ingredient.

EXAMPLE 38

Tablet with Combination of Active Ingredients

The tablet composition is compounded from the following ingredients:

| | |
|---|---|
| 1-(2-Cyano-4-cyclobutylcarbonylamino-phenoxy)-3-tert.butylamino-propan-2-ol | 35.0 parts |
| 2,6-Bis-(diethanolamino)-4,8-dipiperidinopyrimido-[5,4-d]pyrimidine | 75.0 parts |
| Lactose | 164.0 parts |
| Corn starch | 194.0 parts |
| Colloidal silicic acid | 14.0 parts |
| Polyvinyl pyrrolidone | 6.0 parts |
| Magnesium stearate | 2.0 parts |
| Soluble starch | 10.0 parts |
| | 500.0 parts |

Preparation:

The active ingredients, the lactose, corn starch, colloidal silicic acid and polyvinyl pyrrolidone are thoroughly mixed, and the mixture is granulated in the usual way, using an aqueous solution of the soluble starch. The granulate is mixed with the magnesium stearate, and the composition is compressed into 500 mg-tablets, each containing 35 mg of the first active ingredient and 75 mg of the second active ingredient.

Any one of the other compounds embraced by formula I or a non-toxic, pharmacologically acceptable acid addition salt thereof may be substituted for the particular active ingredient of the formula I in Examples 34 through 38. Likewise, the amount of active ingredient in these illustrative examples may be varied to achieve the dosage unit range set forth above, and the amounts and nature of the inert pharmaceutical carrier ingredient may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

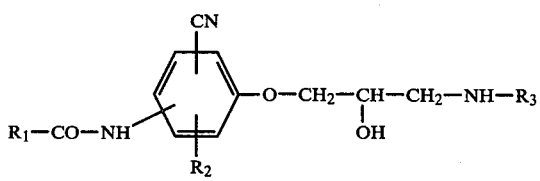

wherein $R_1$ is cycloalkyl of 3 to 10 carbon atoms; phenyl; mono- or poly-substituted phenyl, where the substituents are halogen, lower alkyl, lower alkoxy, lower alkenyl, lower alkinyl, lower alkinyloxy, lower cycloalkyl, acyl, acyloxy, lower alkoxycarbonyl, hydroxy-lower alkyl, lower alkoxy-lower alkyl or the ring-forming groups (—CH=CH—)$_2$ or —O—CH$_2$—O— attached to vicinal carbon atoms of the phenyl ring; aryl-oxy-lower alkyl; (mono- or poly-substituted aryl)-oxy-lower alkyl, where the substituents are halogen, lower alkyl, lower alkoxy, lower alkenyl, lower alkinyl, lower alkinyloxy, lower cycloalkyl, acyl, acyloxy, lower alkoxycarbonyl, hydroxy-lower alkyl, lower alkoxy-lower alkyl or the ring-forming groups (—CH=CH—)$_2$ or —O—CH$_2$—O— attached to vicinal carbon atoms of the phenyl ring;

$R_2$ is hydrogen, halogen, alkyl of 1 to 4 carbon atoms, alkoxy of 1 to 4 carbon atoms or the ring-forming group (—CH=CH)$_2$ or —(CH$_2$)$_n$—, where n is an integer from 3 to 5, attached to vicinal carbon atoms of the phenyl ring; and $R_3$ is straight or branched alkyl of 1 to 10 carbon atoms;

or a non-toxic, pharmacologically acceptable acid addition salt thereof.

2. A compound of claim 1, wherein $R_1$ is substituted phenoxy-methyl or lower cycloalkyl;

$R_2$ is hydrogen; and $R_3$ is alkyl branched adjacent to the amino group;

or a non-toxic, pharmacologically acceptable acid addition salt thereof.

3. A compound of claim 1, which is of the formula

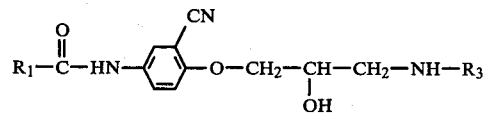

wherein $R_1$ is cycloalkyl of 3 to 6 carbon atoms, phenyl, methylphenoxy-methyl, halophenoxy-methyl, methylphenyl, halophenyl or methoxyphenyl; and $R_3$ is branched alkyl of 3 to 4 carbon atoms;

or a non-toxic, pharmacologically acceptable acid addition salt thereof.

4. A compound of claim 1, which is 1-[2-cyano-4-(3'-methylphenoxyacetylamino)-phenoxy]-3-tert.butylamino-propan-2-ol, or a non-toxic, pharmacologically acceptable acid addition salt thereof.

5. A compound of claim 1, which is 1-(2-cyano-4-cyclobutylcarbonylamino-phenoxy)-3-tert.butylamino-propan-2-ol, or a non-toxic, pharmacologically acceptable acid addition salt thereof.

6. A pharmaceutical composition consisting essentially of an inert pharmaceutical carrier and a therapeutically effective amount of a compound of claim 1.

7. The method of treating tachycardia in a warm-blooded animal in need thereof, which comprises perorally, parenterally or rectally administering to said animal an effective amount of a compound of claim 1.

8. The method of treating hypertension in a warm-blooded animal in need thereof, which comprises perorally, parenterally or rectally administering to said animal an effective amount of a compound of claim 1.

9. The method of treating coronary diseases in a warm-blooded animal in need thereof, which comprises perorally, parenterally or rectally administering to said animal an effective amount of a compound of claim 1.

* * * * *

UNITED STATES PATENT AND TRADEMARK OFFICE
CERTIFICATE OF CORRECTION

PATENT NO. : 4,442,120
DATED : April 10, 1984
INVENTOR(S) : Herbert Koppe et al.

It is certified that error appears in the above-identified patent and that said Letters Patent is hereby corrected as shown below:

Column 2, lines 40 to 59: These lines should be corrected to read:

-- X is -CO-, -$CH_2$- or -CH-lower alkyl, for example with sodium hydroxide or potassium hydroxide in water or in a mixture of ethanol and water.

<u>Method C</u>

By reacting a compound of the formula

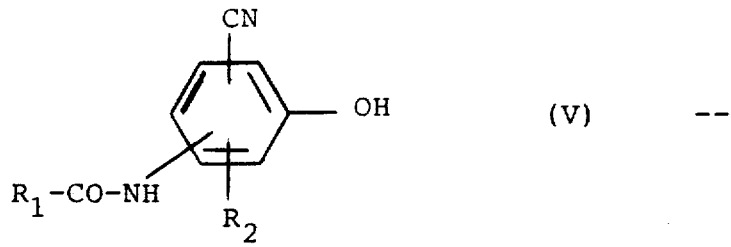

(V)     --

𝔖igned and 𝔖ealed this

Twelfth 𝔇ay of March 1985

[SEAL]

Attest:

DONALD J. QUIGG

*Attesting Officer*     *Acting Commissioner of Patents and Trademarks*